(12) United States Patent
Snyder

(10) Patent No.: US 6,471,962 B1
(45) Date of Patent: Oct. 29, 2002

(54) MONOCLONAL ANTIBODIES FOR INFECTIOUS BURSAL DISEASE, VACCINES AND ASSAYS FOR USE THEREWITH

(75) Inventor: David Snyder, Bowie, MD (US)

(73) Assignee: The University of Maryland, College Park, MD (US)

( * ) Notice: Subject to any disclaimer, the term of this patent is extended or adjusted under 35 U.S.C. 154(b) by 0 days.

(21) Appl. No.: 07/956,473

(22) Filed: Oct. 2, 1992

Related U.S. Application Data

(63) Continuation of application No. 07/423,752, filed on Oct. 18, 1989, now abandoned, which is a continuation-in-part of application No. 07/061,083, filed on Jun. 12, 1987, now Pat. No. 4,956,452, and a continuation-in-part of application No. 07/227,311, filed on Aug. 2, 1988, now Pat. No. 5,064,646.

(51) Int. Cl.[7] ................................................ A61K 39/42
(52) U.S. Cl. .................. 424/147.1; 435/70.21; 435/339; 530/388.3
(58) Field of Search ...................... 530/388.3; 424/85.8, 424/89, 147.1; 435/172.2, 240.27, 70.21, 339

(56) References Cited

PUBLICATIONS

Becht et al., J. Gen. Virol. 69: 631–640, 1988.*
Becht et al., Biol. Abs. 85 (12): 128916.*

* cited by examiner

*Primary Examiner*—Donna Wortman
(74) *Attorney, Agent, or Firm*—Oblon, Spivak, McClelland, Maier & Neustadt, P.C.

(57) ABSTRACT

Two monoclonal antibodies which neutralize all infectious bursal disease viruses are employed in the preparation of infectious bursal disease vaccines. A panel of monoclonal antibodies can be used to characterize the infectious bursal disease virus strains present, according to neutralization site characteristics.

8 Claims, No Drawings

MONOCLONAL ANTIBODIES FOR INFECTIOUS BURSAL DISEASE, VACCINES AND ASSAYS FOR USE THEREWITH

RELATED APPLICATIONS

This application is Continuation of application Ser. No. 07/4223,752, filed on Oct. 18, 1989 now abandoned, which is a CIP of Ser. No. 07/061,083, filed Jun. 12, 1987, U.S Pat. No. 4,956,452, and a CIP of Ser. No. 07/227,311, filed Aug. 2, 1988, U.S. Pat. No. 5,064,696.

BACKGROUND OF THE INVENTION

1. Field of the Invention

This invention pertains to the diagnosis and treatment of infectious bursal disease in poultry, particularly chickens. Specifically, a novel virus and monoclonal antibodies (MCAs) are identified which can be used in the diagnosis of, and prevention of, infectious bursal disease infection of a variety of types.

2. History of the Invention

In 1987, research into infectious bursal disease (IBD) viral infections that were not contained by conventional passive transfer of maternal antibodies or inoculation with a virulent strains resulted in the identification of two neutralizing antibodies, designated R63 and B69, expressed by cell lines deposited at the ATCC under Deposit Nos. 9490 and 9437, respectively, that can be used to prepare vaccines against the virus (IBDV). This work is disclosed in parent U.S. patent application Serial No. 07/061,083, filed June 12, 1987, the entire disclosure of which is incorporated herein by reference.

Subsequent testing of these MCAs identified the development of a new variant IBDV strain not neutralized by these two MCAS. A combination of neutralizing and non-neutralizing but group specific reactive antibodies can be used to identify the presence of the new strain, designated GLS. This work is fully disclosed in parent U.S. application Ser. No. 07/227,311, filed Aug. 2, 1988, the entire disclosure of which is incorporated herein, by reference.

The inventor has now developed a panel of MCAs capable of determining the presence of IBDV, the strain type or types present, and mixture of strains, if present. This panel includes, four additional MCAs which may be employed for use as a diagnostic. Three new MCAs may be used in the preparation of a IBDV vaccine.

SUMMARY OF THE INVENTION

Through processes similar to those developed in parent U.S. application Ser. No. 07/061,083, a panel of MCAs have been established which can be selectively combined to detect the presence of IBD in a poultry flock, and determine the type of strain or the mix of strains, if present. Two of these, MCA 179 and 8 are group reactive and neutralizing to all previously known IBDV. These antibodies are expressed by cell lines deposited at the ATCC, pursuant to the Budapest Treaty, under Deposit Nos. HB-10158 and HB-10174, respectively.

Additionally, the previously identified IBDV strains were reanalyzed, according to specific binding/neutralizing sites present or deleted and classified into one of three groups. Thus, "older" strains, all neutralized by MCA B69, were characterized as "classic". All isolates in this class were collected prior to 1985. Certain post-1985 strains apparently lost the MCA B69 neutralization site, but retained the R63 site (also present in the "classic" group). These were termed the "Delaware" type IBDVs. The third major population of IBDV tested have also lost the R63 binding site. This is the "GLS" type addressed in U.S. application Ser. No. 07/227,311. MCA 179 neutralizes all three classes, as does MCA 8. All MCA sites defined can be shown to be unique in AC-ELISA and competitive binding assays.

The identification of additional monoclonal antibodies that are Delaware or GLS specific allows the determination of the specific type of mixture of IBDV present, and allows the preparation and administration of a suitably responsive vaccine. Thus, MCA 57 expressed by the cell line deposited at the ATCC under Deposit No. HB-10156, is specific for the "GLS" strain. MCA BK9 is specific for the "Delaware" type IBDV. This MCA is expressed by the cell line deposited at the ATCC and accessed by Deposit No. HB-10157.

As noted, MCA B69 specifically neutralizes "classic" type viral strains. Given these three MCAs, the type of IBDV present can be identified. These infections can be prevented with vaccines prepared for the population, either generally, or in light of specific infection. General treatment vaccines can be prepared by using group specific neutralizing antibodies.

DETAILED DESCRIPTION OF THE INVENTION

To determine the type of IBDV infection present, a panel of MCAs is exposed to the bursal samples of the poultry investigated. As a control, a non-neutralizing but group specific antibody, B29, expressed by the cell line deposited under ATCC No. HB 9746 (disclosed in parent U.S. application Ser. No. 07/227,311) can be used to assay for the positive presence of IBDV, per se. The above-described antibodies were used as a panel, in repetitive AC-ELISA assays, performed in a manner similar to that disclosed in U.S. application Ser. No. 07/227,311, to characterize over 870 isolates obtained from poultry sources throughout the United States. The results are set forth in Table I.

TABLE I

| MCA PANEL | AC-ELISA RESULTS | # ISOLATES | CLASSIFICATION |
|---|---|---|---|
| B29 | + | | |
| 179 | + | | |
| 8 | + | | |
| R63 | + | | |
| B69 | + | | |
| BK9 | − | | |
| 57 | − | 60 | Pure Classic |
| B29 | + | | |
| 179 | + | | |
| 8 | + | | |
| R63 | + | | |
| B69 | − | | |
| BK9 | + | 76 | Pure Delaware |
| 57 | − | | |
| B29 | + | | |
| 8 | + | | |
| R63 | − | | |
| B69 | − | | |
| BK9 | − | | |
| 57 | + | 70 | Pure GLS |
| B29 | + | | |
| 179 | + | | |
| 8 | + | | |
| R63 | + | | |
| B69 | + | | |
| BK9 | + | | |
| 57 | + | 5 | Classic + Del + GLS |

TABLE I-continued

| MCA PANEL | AC-ELISA RESULTS | # ISOLATES | CLASSIFICATION |
|---|---|---|---|
| B29 | + | | |
| 179 | + | | |
| 8 | + | | |
| R63 | + | | |
| B69 | + | | |
| BK9 | + | | |
| 57 | − | 21 | Classic + Del |
| B29 | + | | |
| 179 | + | | |
| 8 | + | | |
| R63 | + | | |
| B69 | + | | |
| BK9 | − | | |
| 57 | + | 2 | Classic + GLS |
| B29 | + | | |
| 179 | + | | |
| 8 | + | | |
| R63 | + | | |
| B69 | − | | |
| BK9 | + | | |
| 57 | + | 16 | Del + GLS |

The above results not only confirm the IBDV differentiation described above, that is, the existence of different types of variants of IBDV (sub-types) with a differing number of neutralization sites confirming the utility of the identified panel, but suggests something about the development of the strain. (It should be noted that BK9 and B29 are not neutralizing, but positive indications). Thus, rarely are GLS and Classic mixes in the absence of Delaware strain, found. Classic and Delaware strains, on the one hand, and Delaware and GLS strains, on the other hand, are frequently mixed. This likely indicates a viral evolution pattern of first classic type, followed by Delaware type, in which the B69 neutralization site was lost. From the Delaware strains, the GLS type developed, in which both the B69 and R63 neutralization sites were lost. This history, together with the tabulated results, indicates the GLS strain will be dominant IBDV strain, if it is not dominant already.

Conventionally available vaccines will not satisfactorily control GLS IBDV infection. In fact, it appears that conventional vaccines will not control Delaware infection either. Nine commercially available USDA licensed, live attenuated vaccines were tested against a panel of seven MCAs of B29, B63, B69, 179, BK9, 8 and 57. R63, B69, 8, 179 and 57 are neutralizing types. All nine vaccines gave identical AC-ELISA results. MCAs B29, R63, B69, 8 and 179 all reacted with the antigen (avirulent) of the vaccine, while neither BK9, specific for Delaware, nor 57, specific for GLS and GLS derived viruses, reacted. These results confirmed the vaccines to be drawn from classic type viruses.

To confer resistance to field challenge from Delaware and GLS type IBDV strains, an alternative vaccine is required. While a vaccine comprised of MCA R63 as the active agent will confer protection against classic and Delaware strains, obviously, given its near-dominant nature, GLS infection protection must be provided. Since both 179 and 8 are group reactive and neutralizing, a vaccine prepared using these antibodies as the active agent will confer protection against all three types. Given its greater specificity, MCA 8 is preferred.

The vaccines can be prepared and used in the same way set forth for use of R63 antibodies in Ser. No. 07/061,083.

Although concentrations will vary, depending on poultry type, bird age, geographic and climatic conditions, etc., an effective dosage range of one microgram to one milligram of MCA in a physiologically acceptable carrier, such as buffered saline, cell culture medium, Mareti's virus vaccine diluent, etc. should be effective in conferring protection on one-day old chicks, for a period of two-three weeks, at which time the bird is more immunologically competent. The dosage can be administered once, or repeatedly, in smaller amounts. A preferred dosage range for MCA 179 or 8 appears to be about 20–175 micrograms. As with the R63 and B69 antibodies, the birds are also apparently primed for an active homologous immune response by the vaccine. Repeat injections at times well subsequent to the initial treatment induce what appears to be an anti-idiotype response, followed by an anti-anti-idiotype (antibody) response, which is anti-IBDV, even in the absence of viral injection or infection in the individual.

The invention set forth above has been described with regard to specific examples and general description. Alterations therefrom, particularly with regard to carrier type, dosage range, etc., will not depart from the invention, save as limited by the claims appended hereto. Further, the invention has been extensively described and illustrated with regard to discussion of specific monoclonal antibody strains. Minor modification of the antibody, the cell line expressing the antibody, etc., without effecting the basic neutralizing or binding characteristics of those monoclonal antibodies, similarly is within the skill of those in the art, and does not depart from the scope of the inventive claims appended hereto.

What is claimed is:

1. A monoclonal antibody which neutralizes GLS infectious bursal disease virus (IBDV) and at least one other infectious bursal disease virus type.

2. A monoclonal antibody which neutralizes GLS infectious bursal disease virus (IBDV) and at least one other infectious bursal disease virus type, expressed by cell line ATCC HB-10158.

3. A monoclonal antibody which neutralizes GLS infectious bursal disease virus (IBDV) and at least one other infectious bursal disease virus type, expressed by cell line ATCC HB-10174.

4. A pharmaceutical composition, comprising a pharmaceutically acceptable carrier, and, as an active ingredient, a monoclonal antibody selected from the group consisting of the monoclonal antibody of claim 1, the monoclonal antibody of claim 2, and the monoclonal antibody of claim 3.

5. The composition of claim 4, wherein said active agent is present in an amount of 1 μm–1 mg.

6. A method of providing protection for infant chickens against infectious bursal disease infection, comprising:

inoculating one-day old chickens with a single dose of the composition of claim 4.

7. The method of claim 6, wherein said protection method is employed to prime said chickens for a homologous immune response to IBDV.

8. A cell line expressing the IBDV-specific monoclonal antibody of a cell line selected from the group consisting of ATCC deposits HB-10158-10174, HB-10157 and HB-10156.

* * * * *